United States Patent [19]

Engeler

[11] 4,154,113
[45] May 15, 1979

[54] ULTRASONIC IMAGING SYSTEM
[75] Inventor: William E. Engeler, Scotia, N.Y.
[73] Assignee: General Electric Company, Schenectady, N.Y.
[21] Appl. No.: 908,909
[22] Filed: May 24, 1978
[51] Int. Cl.$^2$ ............................................. G01N 29/00
[52] U.S. Cl. ..................................... 73/626; 128/660; 340/5 MP
[58] Field of Search ................ 73/602, 620, 625, 626, 73/628; 340/1 R, 3 R, 5 R, 5 MP; 128/2 V, 2.05 Z

[56] References Cited

U.S. PATENT DOCUMENTS

| | | | |
|---|---|---|---|
| 3,918,024 | 11/1975 | Macovski | 340/5 MP |
| 4,005,382 | 1/1977 | Beaver | 73/626 |
| 4,012,952 | 3/1977 | Dory | 73/626 |
| 4,058,003 | 11/1977 | Macovski | 340/1 R |
| 4,079,352 | 3/1978 | Burckhardt et al. | 340/1 R |

Primary Examiner—Stephen A. Kreitman
Attorney, Agent, or Firm—Julius J. Zaskalicky; Joseph T. Cohen; Marvin Snyder

[57] ABSTRACT

A real time ultrasound imaging system which includes coherent demodulation of echo signals followed by time delay and coherent summation of the demodulated signals is described. As the range from which echoes are being received increases, coherent demodulation is maintained. Demodulation and time delay accuracies are relatively easy to maintain over a large field of view and a long range. The system has high resolution and high sensitivity.

5 Claims, 26 Drawing Figures

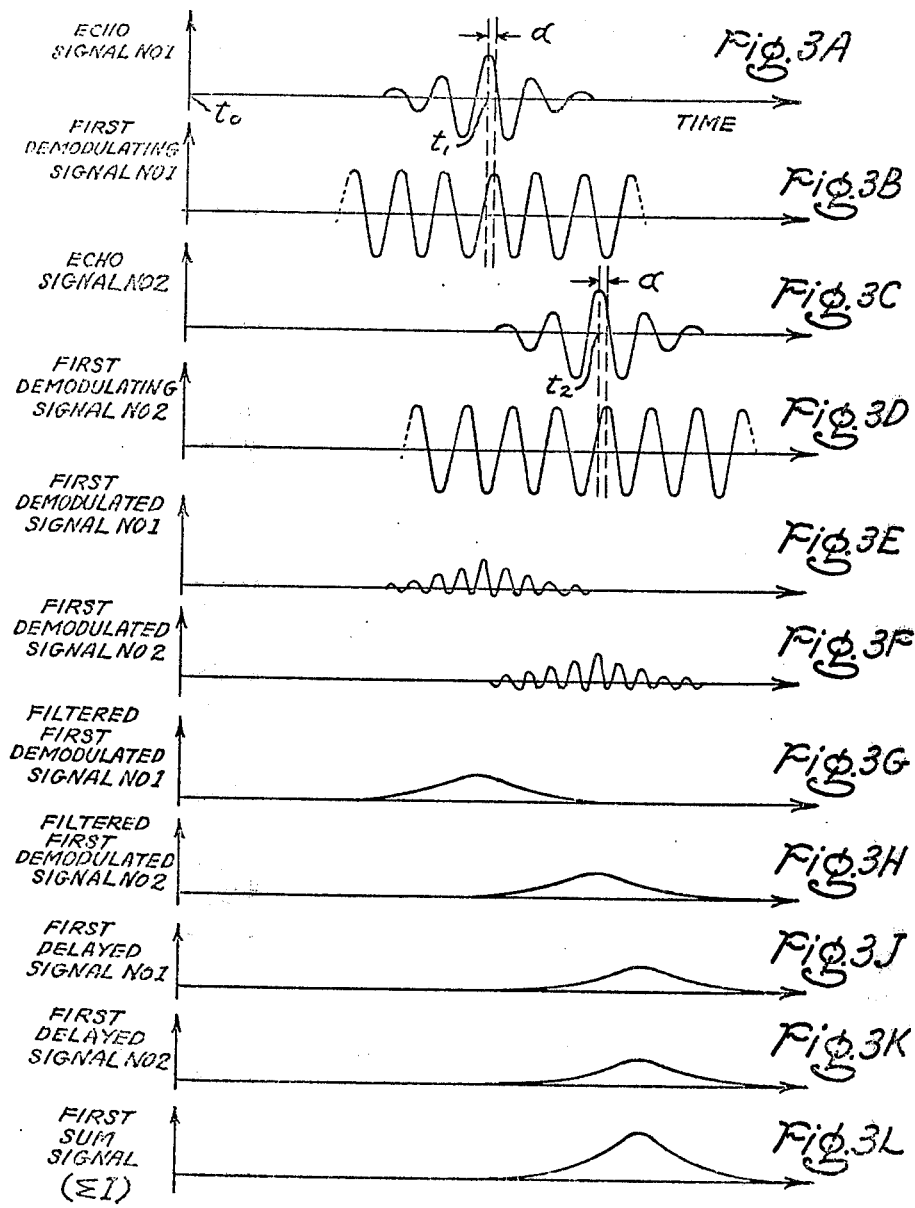

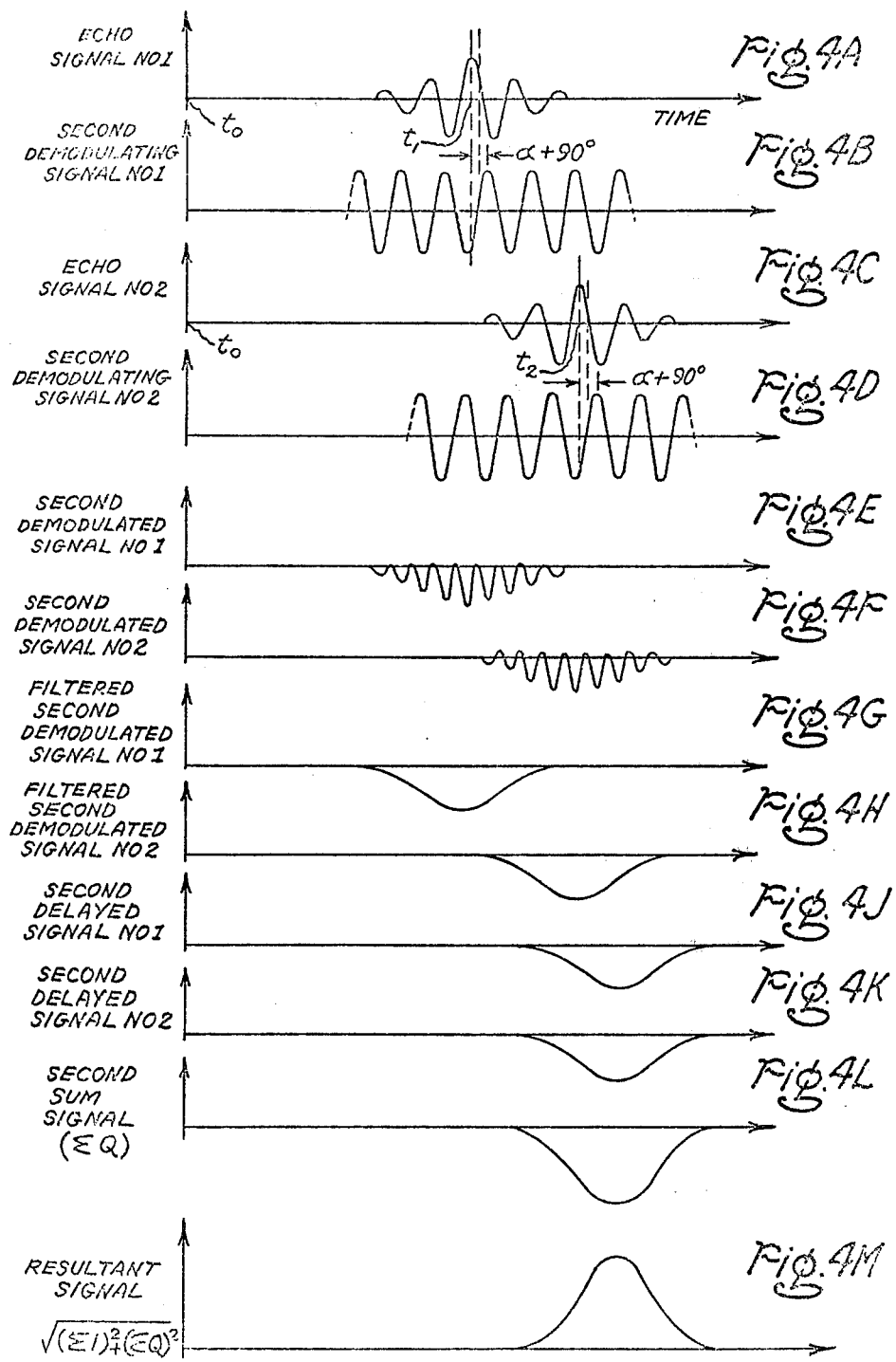

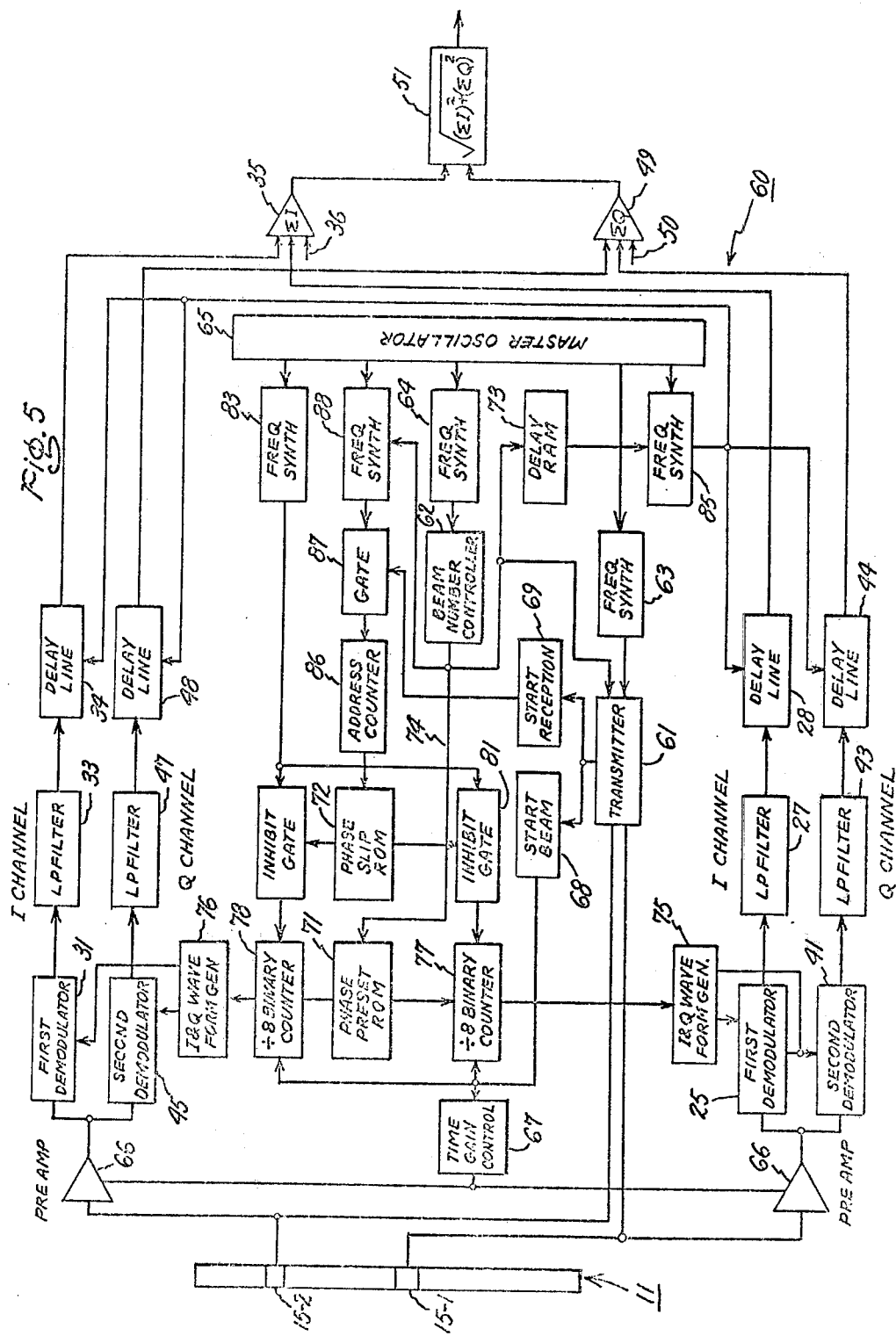

ULTRASONIC IMAGING SYSTEM

The present invention relates to apparatus for ultrasonic imaging and more particularly to signal processing sub-systems therefor.

This application is related to U.S. Pat. application Ser. No. 908,908 filed concurrently herewith and assigned to the assignee of the present application.

Ultrasonic imaging systems for imaging object points such as soft tissue features of the human body comprise in general an array of transmitting transducers and an array of receiving transducers. The transducers are constituted of piezoelectric materials which emit ultrasound in response to electrical excitation and conversely provide an electrical signal in response to ultrasound impinging thereon. The transmitting and receiving arrays may be identical. The resonant frequencies of the transducers of the transmitting and receiving arrays are substantially identical. The transducers of the transmitting array are excited in sequence by electrical pulses to generate a burst of ultrasound consisting of several cycles of oscillation at the resonant frequency of the transducers. The burst of ultrasound is coupled into the space or object region surrounding the array. The burst of ultrasound impinging on object points in the object region produce echoes which are reflected and received by the transducers of the receiving array and generate therein echo signals which are typically of a few cycles duration. The echo from an object point arrives at the receiving transducers at different times due to the differences in time of propagation of the echo from the object point to the transducers. In prior art systems, the echo signals generated by the receiving transducers are respectively delayed so that all echo signals emanating from a particular object point are of like phase, and are then coherently summed. The sum signal is then envelope detected and displayed on a suitable display device.

Physical constraints of ultrasonic transducers make it difficult to achieve resonant Q's less than about two or three. Thus, the burst of ultrasound, even when impulse drive is utilized on the transducers, typically consists of a number of cycles. For a sampled data system, sampling at several times the resonant frequency of the transducers is required. This necessitates long, high speed shift registers to provide the requisite delays to effect coherent summation of the received electrical signals. Furthermore, the accuracy of the time delay must correspond at least to about $\frac{1}{4}$ to $\frac{1}{2}$ of one cycle of the resonant frequency period.

The present invention is directed to providing improvements in such prior art ultrasonic imaging apparatus.

An object of the present invention is to provide improvements in the performance of real time ultrasonic imaging systems, particularly with regard to lateral resolution thereof.

Another object of the present invention is to provide improvements in the field of view of high resolution ultrasound imaging systems.

Another object of the present invention is to provide in ultrasound imaging systems a large depth of field without any discontinuities in the image.

A further object of the present invention is to provide an ultrasound imaging system which is tolerant of time delay errors in the time delay compensating devices thereof.

In carrying out the invention in one illustrative embodiment thereof there is provided a means for producing and directing a burst of ultrasound of a predetermined frequency into an object region. An array of transducers is provided to receive echoes of ultrasound produced by the burst of ultrasound impinging on object points in the object region. Each echo from a respective object point produces in the transducers a respective set of electrical signals, one electrical signal in each transducer. The time of occurrence of each of the electrical signals is dependent on the distance between a respective transducer and the respective object point. Means are provided for demodulating the electrical signals obtained from the transducers including mixing each of the electrical signals with first and second demodulating signals of substantially the same frequency as the aforementioned predetermined frequency but in phase quadrature relationship thereto to obtain a plurality of pairs of demodulated signals. Means are provided for delaying each pair of demodulated signals by a respective predetermined interval of time corresponding to the distance between a respective transducer and the respective object point to cause each pair of first and second demodulated signals to occur at the same time. A first sum means is provided for summing the delayed first demodulated signals to obtain a first sum signal. A second sum means is provided for summing the delayed second demodulated signals to obtain a second sum signal. A means is provided for forming a resultant signal which is monotonic function of the sum of the square of the first sum signal and the square of the second sum signal.

The novel features which are believed to be characteristic of the present invention are set forth with particularity in the appended claims. The invention itself, both as to its organization and method of operation, together with further objects and advantages thereof may best be understood by reference to the following description taken in connection with the accompanying drawings wherein:

FIGS. 3A through 3L are diagrams of amplitude vs. time of voltage signals occurring at various points in the sub-system of FIG. 2 associated with the I channels thereof. The point of occurrence of a signal of FIGS. 3A through 3L in the block diagram of FIG. 2 is identified in FIG. 2 by the letter of the figure designation of the signal.

Figure 2:
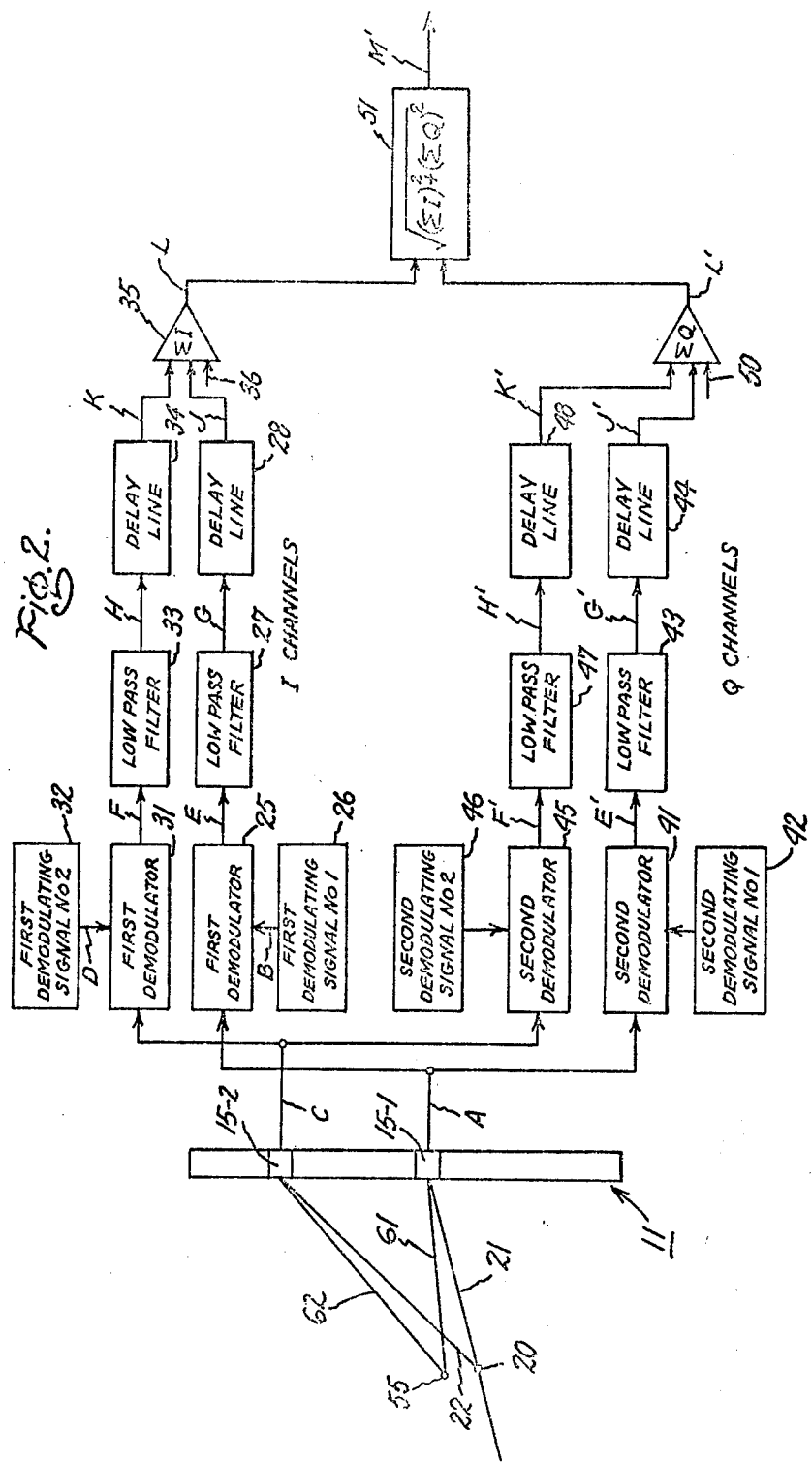
FIG. 2 is a functional block diagram of a sub-system of an ultrasound imaging system useful in explaining the principles of the present invention.

FIGS. 4A through 4L are also diagrams of amplitude vs. time of voltage signals occurring at various points in the sub-system of FIG. 2 associated with the Q channels thereof. FIG. 4M is a diagram of the resultant signal formed from the signals of FIGS. 3L and 4L. The point of occurrence of a signal of FIGS. 4A through 4M in the block diagram of FIG. 2 is identified in FIG. 2 by the letter primed of the figure designation of the signal.

FIG. 5 is a functional block diagram of the ultrasonic imaging system embodying the present invention.

Figure 1:
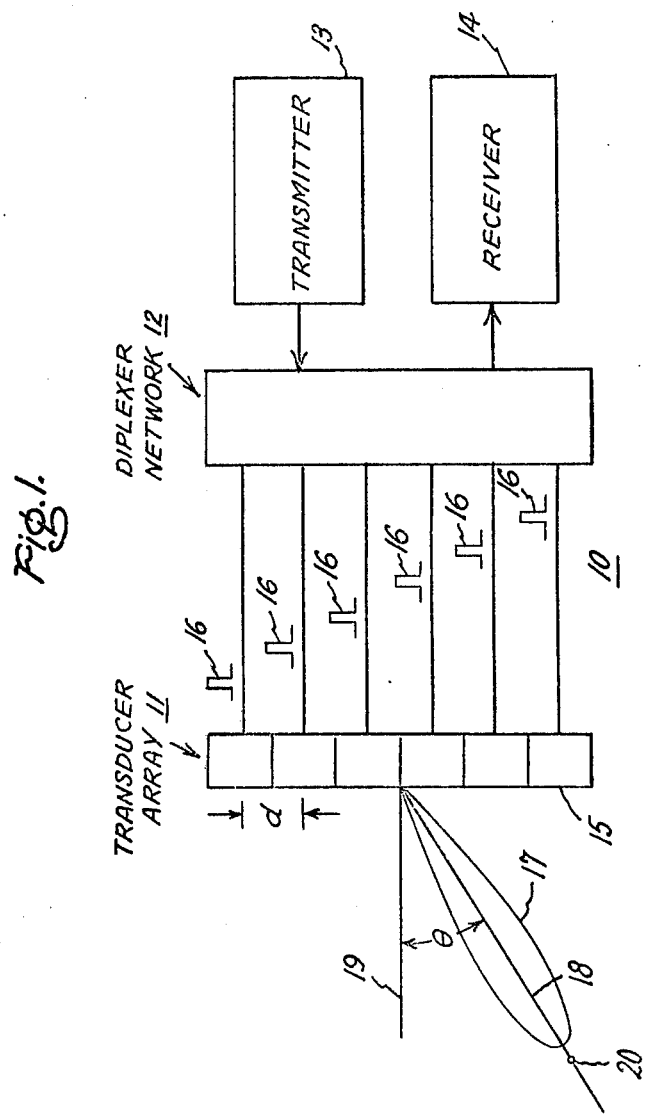
FIG. 1 is a block diagram illustrating the operation of an ultrasound imaging system.

Reference is now made to FIG. 1 which shows a block diagram of the general organization of an ultrasonic imaging system 10 in accordance with one embodiment of the present invention. The ultrasonic imaging system 10 includes a transducer array 11, a diplexer network 12, a transmitter 13 and a receiver 14. In this embodiment of the invention the transducer array 11 is a linear array and includes a plurality of equally spaced transducer 15 having a center-to-center spacing of d. As shown, the transducer array functions as both a transmitting array and a receiving array. The transmitter 13 develops a sequence electrical pulses 16 which are applied through the diplexer network 12 to the transducer 15. The bursts of ultrasound generated in the transducers 15 emanate into an object region adjacent the array. In the aggregate the bursts of ultrasound are directed in a preselected azimuthal direction dependent upon the linear timing sequence of the pulses 16. The variation of the intensity or amplitude of the burst of ultrasound in azimuth about the mid-point of the array is referred to as the beam of the array. The beam 17 of array 11 is shown as having an axis 18 making an angle $\theta$ with the normal 19 to the midpoint of the array 11. The relationship between the time delay increment $T_i$, which is added successively to each $i^{th}$ signal from end (i=1) of the array to the other end (i=n) to exactly compensate for the propagation path time delay differences that exist under plane wave conditions is given by the following relationship:

$$T_i = (i-1)d \sin \theta / c, \qquad (1)$$

where c is the velocity of ultrasound in the object region adjacent the array.

By progressively changing the time delay between successive excitation pulses, the angle $\theta$ on one side of the normal 19 is changed by increments to form and steer the transmitted beam to successive scan line directions comprising the image. On the other side of the normal 19 the timing of the excitation pulses 16 is reversed so that the transducers are energized in reverse order. Echoes produced by the bursts of ultrasound impinging on targets in the object regions, such as target or object point 20, are sensed by the transducers 15 at different times due to the differences in the propagation paths from the object point 20 to the transducers. Echo signals produced in transducers 15 by the echoes are passed through the diplexer network 12 to the receiver 14 where they are amplified to a roughly constant level. To simultaneously sum the electrical signals produced by an echo from an object point, time delays are introduced into the signal processing channels of the receiver associated with the transducers 15. In the case of a linear array the delay introduced in each channel associated with a respective transducer may be subdivided into two components, one referred to as a beam steering time delay and the other referred to as a focusing time delay. The beam steering time delays for reception are the same as the beam steering time delays for transmission. Focusing time delays are introduced into each of the channels to compensate for propagation path delay differences from the object point 20 to the various transducer positions in the array. The focusing delay increment for each transducer is given by the equation:

$$T_k = a^2 / 2Rc [1 - (x_k/a)^2] \cos^2 \theta \qquad (2)$$

where
 a = the half-aperture distance of the array,
 R = the focal distance or range to the object point,
 c = the velocity of ultrasound in the object region,
 $x_k$ = the distance from the center of the array to the $k^{th}$ element, and
 $T_k$ = the time delay associated with the signal from the $k^{th}$ element to coherently sum the electrical signals produced by an echo from object point 20.

It will be understood that the ultrasound echo arrives first at the center transducer of the array and last at the end transducers, the greatest delay is provided to the echo signal from center transducer. Also, it will be understood that the delay for the echo signal from a transducer varies as the cosine squared of the beam angle as the apparent width of the aperture varies as the cosine of the beam angle $\theta$. The receiving focus can be dynamically changed to track the range from which echoes are being received during the echo reception period. The pulses 16 are periodically repeated at a rate referred to as the pulse repetition rate and provide corresponding echo pulses from an object point to each of the transducers which provide echo signals in each of the channels of the receiver. By progressively changing the time delay between successive excitation pulses and by progressively changing the time delay associated with the received signals, the angle $\theta$ of the beam 17 is changed by increments. The signals developed at the output of the receiver are suitably displayed on an oscilloscope (not shown) to provide a display of the object region which may be a portion of a human body, for example. Other array configurations may also be used, provided the appropriate time delay compensation is utilized to coherently sum the echoes emanating from an object point.

Reference is now made to FIG. 2, which shows a functional block diagram of apparatus in an ultrasound imaging system for processing echo signals in accordance with an embodiment of the present invention. The apparatus includes an array 11 of transducers 15 having substantially the same resonant frequency. For simplicity of explanation, array 11 is shown as a linear array, but might have any other suitable shape. Point 20 represents an object point in an object region surrounding the array. A burst of several cycles of ultrasound produced by the array impinges upon the object point 20 and generates an echo. The burst produced by a plurality of transducers of the array may be considered to originate at the center of the array. The echo is received at various transducers of the array at different times depending upon the distances between the object point 20 and the transducers of the array. Such an echo produces a set of echo signals in the transducers elements—one in each transducer. The processing of echo signals generated in transducers 15-1 and 15-2 will be particularly described. It will be understood that the echo signals generated in the other transducers are similarly processed. Transducer 15-1 is located at the center of the array and transducer 15-2 is located above the center of the array. Line 21 represents the propagation path of the echo reflected from object point 20 to the center of transducer 15-1. Line 22 represents the propagation path of the echo reflected from object point 20 to transducer 15-2.

The echo signal generated in the transducer 15-1 is referred to as echo signal No. 1 and the echo signal generated in transducer 15-2 is referred to as echo signal No. 2. Each of echo signals No. 1 and 2 as well as the echo signals generated in each of the other transducers of the array are processed in a respective signal processing channel, referred to as an I channel. Each of the I channels performs the functions of demodulation, filtering, and delay. Each of echo signals No. 1 and 2 as well as the other echo signals generated in the other transducers of the array are also processed in a respective Q signal processing channel in which the functions of demodulation, filtering, and delay are also provided. The demodulating signal utilized in each of the Q channels is set to be in phase quadrature relationship with respect to the demodulating signal utilized in the demodulation process in a respective I channel. The delayed signals in the I channels are coherently summed to obtain a first sum signal and the delayed signals in the Q channels are also coherently summed to obtain a second sum signal. From the first sum signal and the second sum signal a resultant signal is developed representing the reflection from the object point 20.

Reference is not made additionally to FIGS. 3A through 3L. The point of occurrence of a signal of FIGS. 3A through 3L in the block diagram of FIG. 2 is identified in FIG. 2 by the letter of the figure designation of the signal. Echo signal No. 1 generated in transducer 15-1 is shown in FIG. 3A. The peak of echo signal No. 1 occurs at a time $t_1$ after the time of occurence $t_0$ of the peak of the burst of ultrasound launched by the array. The time of occurrence $t_1$ of the peak of the echo signal No. 1 depends on the distance 21 between the object point 20 and the transducer 15-1. Echo signal No. 1 is applied to a first demodulator 25 to which source 26 also applies first demodulating signal No. 1, shown in FIG. 3B. First demodulating signal No. 1 and the other first demodulating signals to be referred to in this description have a fundamental frequency substantially equal to the resonant frequency of the transducers. While the waveform of the first demodulating signals is shown as sinusoidal other waveforms, such as square waveforms, may be used. First demodulating signal No. 1 is shown lagging in phase with respect to echo signal No. 1 by phase displacement $\alpha$. The first demodulator 25 provides at it output first demodulated signal No. 1 shown in FIG. 3E, representing the product of echo signal No. 1 and first modulating signal No. 1. First demodulated signal No. 1 is applied to low-pass filter 27 which recovers the envelope thereof, shown in FIG. 3G. Delay line 28 provides a predetermined delay in the filtered first demodulated signal No. 1 so that similarly processed I channel signals from other transducers of the array occur at the same time and thus can be coherently summed. Delayed filtered first demodulated signal No. 1 is shown in FIG. 3J and is referred to as first delayed signal No. 1.

Echo signal No. 2 generated in transducer 15-2 is shown in FIG. 3C. The peak of echo signal No. 2 is shown as occurring at a time $t_2$ after the time of occurrence $t_0$ of the peak of the burst of ultrasound launched by the array. The time of occurrence $t_2$ of the peak of the echo signal No. 2 depends upon the distance 22 between the object point 20 and the transducer 15-2. Echo signal No. 2 is applied to demodulator 31 to which source 32 applies first demodulating signal No. 2, shown in FIG. 3D. First demodulating signal No. 2 is set lagging in phase with respect to echo signal No. 2 by phase displacement $\alpha$, the same phase displacement utilized in connection with echo signal No. 1 and first demodulating signal No. 1. To meet this requirement and phase of first demodulating signal No. 2 is changed with respect to the phase of first demodulating signal No. 1 by an amount dependent on the difference in propagation distances 21 and 22. First demodulated signal No. 2, shown in FIG. 3F, appears at the output of the first demodulator 31, representing the product of echo signal No. 2 and first demodulating signal No. 2. After filtering by the low-pass filter 33, the envelope of first demodulated signal No. 2, shown in FIG. 3H, is recovered. First demodulated signal No. 2 is delayed by delay line 34 to occur at the same time as the time of occurrence of delayed filtered first demodulated signal No. 1 and the other delayed filtered first demodulated signals of the I channels. Delayed filtered first demodulated signal No. 2 is shown in FIG. 3K and is referred to as first delayed signal No. 2.

First delayed signal No. 1 and first delayed signal No. 2 are summed in sum amplifier 35 to provide a first sum signal, shown in FIG. 3L. Echo signals generated in each of the other transducers of the array are processed in a similar manner and summed as collectively indicated by arrow 36 to provide at the output of sum amplifier 35 a large amplitude signal $\Sigma I$ representing contributions of all of the echo signals generated in the transducers of the array to the first sum signal.

Reference is now made additionally to FIGS. 4A through 4M. The point of occurrence of a signal of FIGS. 4A through 4M in the block diagram of FIG. 2 is identified in FIG. 2 the letter primed of the figure designation of the signal.

Echo signal No. 1 generated in transducer 15-1 is shown in FIG. 4A. As mentioned in connection with FIG. 3A, the peak of echo signal No. 1 occurs at a time $t_1$ after the time of occurrence $t_0$ of the peak of the burst of ultrasound launched by the array. The time of occurrence $t_1$ of the peak of the echo signal No. 1 depends on the distance 21 between the object point 20 and the transducer 15-1. Echo signal No. 1 is applied to a second demodulator 41 to which source 42 also applies second demodulating signal No. 1 shown in FIG. 4B. Second demodulated signal No. 1 and the other second demodulating signals to be referred to in this description have a fundamental frequency substantially equal to the resonant frequency of the transducers. While the waveform of the second demodulating signals is shown as sinusoidal, other waveforms such as square waveforms may be used. Second demodulating signal No. 1 is set to be lagging by 90 degrees the phase of first demodulating signal No. 1 or $\alpha + 90$ degrees lagging in phase the phase of echo signal No. 1. The second demodulator 41 provides at its output second demodulated signal No. 1 shown in FIG. 4E, representing the product of echo signal No. 1 and second demodulating signal No. 1. Second demodulated signal No. 1 is applied to low-pass filter 43 which recovers the envelope thereof, shown in FIG. 4G. Delay line 44 provides a predetermmined delay in filtered second demodulated signal No. 1 so that similarly processed Q channel signals from other transducers of the array occur at the same time and thus can be coherently summed. Delayed filtered sound demodulated signal No. 1 is shown in FIG. 4J and is referred to as second delayed signal No. 1.

Echo signal No. 2 generated in transducer 15-2 is shown in FIG. 4C. As mentioned in connection with FIG. 3C, the peak of the echo signal No. 2 is shown as occurring at a time $t_2$ after the time of occurrence $t_0$ of the peak of the burst of ultrasound launched by the array. The time of occurrence $t_2$ of the peak of the echo signal No. 2 depends upon the distance 22 between the object point 20 and the transducer 15-2. Echo signal No. 2 is applied to second demodulator 45 to which source 46 also applies second demodulating signal No. 2, shown in FIG. 4D. Second demodulating signal No. 2 is set to be lagging by 90 degrees the phase of the first demodulating signal No. 2 or $\alpha + 90$ degrees lagging in phase the phase of echo signal No. 2. Second demodulated signal No. 2, shown in FIG. 4F, appears at the output of the second demodulator 45, representing the product of echo signal No. 2 and second demodulating signal No. 2. Second demodulated signal No. 2 is applied low-pass filter 47 which recovers the envelope of second demodulated signal No. 2, shown in FIG. 4H. Delay line 48 provides a predetermined delay in filtered second demodulated signal No. 2 so that similarly processed Q channel signals from other transducers of the array occur at the same time and thus can be coherently summed. Delayed filtered second demodulated signal No. 2 is shown in FIG. 4K and is referred to as second delayed signal No. 2.

Second delayed signal No. 1 and second delayed signal No. 2 are summed in sum amplifier 49 to provide a second sum signal, shown in FIG. 4L. Echo signals generated in each of the other transducers of the array are processed in a similar manner and summed, as collectively indicated by arrow 50, to provide at the output of sum amplifier 49 a large amplitude signal $\Sigma Q$ representing contributions of all of the echo signals generated in the transducers of the array to the second sum signal.

The first sum signal from the output of sum amplifier 35 and the second sum signal from the output of amplifier 49 are applied to a circuit 51 for deriving a resultant signal which is a monotonic function of the sum of the square of the first sum signal and the square of the second sum signal. More particularly the circuit provides a resultant signal which is proportional to the square root of the sum of the square of the first sum signal and the square of the second sum signal. The circuit 51 provides a resultant signal the amplitude of which is independent of the setting of the phase of each of the first demodulating signals in respect to a respective one of the echo signals, and of course independent of the setting of each of the second demodulating signals in respect to a respective one of the echo signals as each second demodulating signal is set in phase quadrature relationship to a respective one of the first demodulating signals. This result will be readily understood from a consideration of the following example. As the first demodulating signal No. 1 of FIG. 3B lags the phase of the echo signal of FIG. 3A by $\alpha$ degrees, the peak amplitude of the first demodulated signal No. 1 of FIG. 3E is equal to cosine $\alpha$ times the maximum value that the first demodulated signal No. 1 may have corresponding to the situation in which the first demodulating signal No. 1 of FIG. 3B is in phase with the echo signal No. 1 of FIG. 3A. As the second demodulating signal No. 1 of FIG. 4B lags the phase of echo signal No. 1 by $(\alpha + 90)$ degrees, the amplitude of the second demodulated signal No. 1 of FIG. 4E may be represented by the cosine $(\alpha + 90)$ times the maximum possible amplitude that the second demodulated signal No. 1 may have corresponding to the condition in which the second demodulating signal No. 1 is in phase with the echo signal No. 1. To obtain the maximum value of the first demodulated signal No. 1 it is simply necessary to take the square root of the sum of the squares of the first demodulated signal No. 1 and the second demodulated signal No. 1. Noting that $\sqrt{\cos^2 \alpha + \cos^2(\alpha + 90)}$ is independent of $\alpha$ and is equal to one, it is apparent that the maximum value of the first demodulated signal is proportional to the peak of echo signal No. 1. As each of the other echo signals are processed in the same way it is clear that the result illustrated in the above example is valid for the first sum signal $\Sigma I$ and for the second sum signal $\Sigma Q$. In FIG. 3A through 3D the phase displacement or angle $\Sigma$ is shown as 60 degrees. Also in FIG. 4A through 4D the angle $\alpha$ is shown as 60 degrees. Thus, by utilizing a pair of I and Q channels for the processing of each echo signal a resultant signal is obtained which is independent of the angle $\alpha$. However, in order to prevent cancellation when the sum signals are formed, the angle $\alpha$ for each first demodulating signal and a respective echo signal must be substantially the same. This result is accomplished by setting the phase of each of the first demodulating signals with respect to one another so that the relationship of each first demodulating signal with respect to a respective echo signal is substantially the same. The phase setting of each first demodulating signal is dependent on the propagation distance from the object point 20 to a respective transducer. As each second demodulating signal is set in quadrature lagging relationship with respect to a respective first demodulating signal, the proper phase relationship for each of the second demodulating signals is automatically obtained.

The manner in which the apparatus responds to object points in the vicinity of the object point 20 will now be considered. Referring to FIG. 2 consider a neighboring point 55 which is located at the same range from the array as object point 20 but laterally displaced from object point 20 along an arc centered on transducer 15-1. Since the propagation path to transducer 15-1 is the same length, the signal arriving from neighboring point 55 will have the same phase angle $\alpha$ with respect to the demodulating waveform used in demodulators 25 as the signal from point 20. The signals in other transducers, such as transducer 15-2, however, will arrive with different phases compared to the signal from point 20 because the paths, such as distances 61 and 62, are not equal in length. Thus, the phase angle between the signal arriving from point 55 at transducer 15-2 and the demodulating signal applied to first demodulator 31 will not be equal to $\alpha$. Furthermore, the actual phase angle will vary more or less uniformly with the position of the transducer. For each particular transducer the output of the respective demodulator will therefore vary in amplitude and polarity, depending on the position of the transducer. These changes in magnitude and polarity are maintained in the low-pass filters 27 and 33 and through the delay lines 28 and 34. In the sum amplifier 35, the signals coming from all of the transducers are added algebraically, as these are more or less uniformly varying as to magnitude and polarity, the net contribution of echo signals due to an echo from the neighboring point 55 is very small. Through a similar analysis for echo signals from target point 55 processed in the Q channels, the net contribution at the output of the sum amplifier is very small. Thus, in utilizing coherent phase demodulation of echo signals in conjunction with the delay and summation of demodulated signals excellent rejection of echo signals from points in the vicinity of the object point 20 is provided thereby providing high resolution. Echo signals produced in the transducer array by object points located in the range zone of the object point focused on but displaced therefrom are on average cancelled out at the output of the sum amplifier due to coherent phase demodulation and the coherent summation mentioned above. The sensitivity profile of the system to echoes displaced in azimuth from the focal point is called the received beam. In addition, in view of the fact that the bursts of ultrasound are transmitted along a narrow beam and also that echoes received by the transducers of the array are delayed and summed to provide a narrow beam, appreciable angular departure of an object point from the axis of the beam provides echoes at the video output which are considerably attenuated due both to the fact that the full intensity of the beam is not directed at such an object point and that the receiving beam as well is not oriented on such an object point.

For proper operation of the sub-system of FIG. 2 the phase of each first demodulating signal in relation to the phase of a respective echo signal should be substantially the same for all pairs of signals. Of course, the phasing of the second demodulating signals are fixed by the phasing of the first demodulating signals. An object point at a different range would require different relative phasing of the first demodulating signals and also, of course, of the second demodulating signals to obtain the ideal response at the output of the sum amplifiers 35 and 49. For small increments in range from the range of object point 20 the relative phase requirements of the first demodulating signals and of the second demodulating signals do not change sufficiently to cause a significant departure in performance from the performance that would be obtained were the ideal relative phases utilized. However, at some point differing in range from that of object point 20 the changing relationships of the propagation times to the transducers causes performance to become marginal, and it is necessary to provide a new set of relative phase relationships for the first and second demodulating signals to obtain approximately ideal performance. This new set of relative phase relationships would be valid for a certain range span beyond which another set of phase relationships would be provided. In general, as the ultrasound burst moves deeper into the object region, the object point focussed on is caused to track the burst by sequentially adjusting the phase relationships of the demodulating signals in discrete steps or continuously. The manner in which the phases of the first and second demodulating signals may be reset to accommodate the different requirements for relative phase settings with range will be described in connection with the functional block diagram of FIG. 5.

In addition to selecting the correct phase relationships of the demodulating signals, steering a receiving beam in a particular direction, such as along line 21, requires that time delays be provided in each of the I and Q channels, as explained in connection with equation 1 for the case of a linear array. To focus on a particular object point in the direction of a steered receiving beam, each I channel and each Q channel is provided in addition with a respective focusing delay, as described above in connection with equation 2. To maintain focus as echoes are received from more distant object points, the focussing delays may be altered with range.

Successive echoes received from successive object points successively more distant, i.e. at greater ranges, from the array produce successive sets of electrical signals in the transducers of the array 11. Successive sets of first demodulating signals and second demodulating signals would be provided with the proper relative phase relationships as explained above. In addition, the steering and focussing delays provided in the I channels and Q channels would be changed as explained above. The resultant signal appearing at the output of circuit 51 would include elements corresponding to echoes received from the successive object points.

A plurality of bursts of ultrasound may be applied to the array to produce a plurality of echo signals and a plurality of resultant signals at the output of circuit 50. In addition the angle of the transmitting and receiving beams may be incremented after each burst so as to scan from one extreme angle toward one side of the array to the extreme angle toward the other side, and corresponding resultant signals may be obtained. The resultant signals may then be suitably displayed in various scan modes on a display device to provide a visual indication of the tissue structure of the body within the field of view. Sufficient high repetition rates may be used to provide a visual image of moving objects within the human body.

The manner in which the relative phases of the first demodulating signals and the second demodulating signals are pre-set during the period of reception of echoes from an object region and the manner in which the relative phases of the first demodulating signals and the second demodulating signals are changed with range to maintain coherent demodulation will be described in connection with FIG. 5. The manner in which the time delays in each of the I and Q channels are set to obtain receiving beams at various angles which are focussed at various ranges will also be described in connection with FIG. 5.

Reference is now made to FIG. 5 which shows a functional block diagram of an ultrasound imaging system 60 incorporating one embodiment of the invention disclosed and described in connection with FIG. 2. The elements of FIG. 5 identical to the elements of FIG. 2 are identically designated. Transmitter 61 provides pulses of proper duration and timing to the transducers of the linear array 11 to form a transmitting beam which may be oriented along a number of different directions. Each direction or position of the beam is assigned a beam number. Beam numbers for controlling the direction of the transmitting beam are supplied to transmitter 61 from beam number controller 62. Frequencies for the operation of the transmitter 61 and beam number controller 62 are supplied by frequency synthesizer 63 and 64, respectively, connected to master oscillator 65.

A plurality of preamplifiers 66 are provided, each connected between a respective transducer and a respective pair of I and Q signal processing channels to provide echo signals of suitable amplitude for processing. A time gain control circuit 67 provides an output signal to each of the preamplifiers 66 to equalize the amplitudes of the echo signals developed in the various transducers of the array 11 as a function of range to facilitate the processing thereof. The time gain control circuit 67 is activated after each transmitted burst of sound by a start beam signal received from start beam circuit 68 and synchronized with the pulses from transmitter 61. The start beam signal is also utilized to initiate pre-setting of the phases of the I and Q waveform generators of the system, as will be explained below. I and Q waveform generator 75 provides the outputs produced by first demodulating signal generator 25 and second demodulating signal generator 41 of FIG. 2. I and Q waveform generator 76 provides the outputs provided by the first demodulating signal generator 26 and second demodulating signal generator 45. A start reception circuit 69 synchronized with the pulses supplied by the transmitter 61 develops a start reception signal following the occurrence of a start beam signal which is utilized to control a phase slip sequence for the signal processing channels associated with the various transducers of the array, as will also be explained below in greater detail.

It was pointed out above that the initial settings of the relative phase relationships of the first and second demodulating signals for each of the echo signals developed in the array 11 is a function of the direction of the receiving beam. The manner in which the phase of the first and second demodulating signals associated with a particular transducer must be changed with the range from which echoes are being received to obtain coherent demodulation is also a function of the direction of the receiving beam. It was also pointed out above that the delays necessary in each of the signal processing channels to provide coherent summation are also a function of the direction of the receiving beam. Thus, for each receiving beam position a unique set of phase preset data must be supplied to the demodulating circuits of all of the channels, and a unique set of time delay data must be supplied to the delay lines of all of the channels. In general, in a linear array the phase relations implied by equation 1 is independent of range and depends only on beam angle, but those implied by equation 2 are dependent on range and therefore time dependent so that a sequence of time dependent changes of the phase relations is necessary. This is provided by the phase slip schedule. A pairwise unique schedule of phase slip data must be provided, but this can be approximated well by a single set of phase slips provided they are effected at different rates for different directions. In this way, the total phase relationship is separated into a portion that depends only on beam angle and another portion which depends parametrically on beam angle but is otherwise only dependent on range. The portion of the phase relationship that depends only on angle is handled as a phase preset. Phase preset data is derived for each beam number and is stored in phase preset ROM (Read Only Memory) 71. Channel delay data is derived for each beam number and is stored in delay RAM (Random Access Memory) 73. Phase slip data is derived for each beam number and is stored in a phase slip ROM 72. As mentioned above, phase slip data can be collapsed to a single schedule if the schedule is read out at different rates at different angles.

The manner in which the above-mentioned functions are implemented will now be described. First, consider the manner in which the relative phases of the first and second demodulating signals in the various channels is pre-set to provide coherent demodulation for a receiving beam having a particular number. The first and second demodulating signals for echo signal from transducer 15-1 are provided by I and Q waveform generator 75. The first and second demodulating signals for echo signal from transistor 15-2 are provided by I and Q waveform generator 76. Each of the first and second demodulating signals in each of the channels can be preset to any one of eight positions displaced from one another by 45 degrees. The generator 75 is under the control of divide-by-eight binary counter 77. The generator 76 is under the control of divide-by-eight binary counter 78. Any one of eight possible phase positions of each of the divide-by-eight counters is obtained by presetting the divide-by-eight counter by a respective three-bit word. The three-bit words are obtained from the phase preset ROM 71. For each beam number a plurality of three-bit words are stored in ROM 71, each word representing the phase setting of a respective I and Q waveform generator. Thus, on appearance of a beam number on the line 74 from the beam number controller 62, ROM 71 is accessed to provide the proper pre-setting of the divide-by-eight binary counters of all of the channels. On appearance of the start beam signal from start beam circuit 68, the divide-by-eight binary counters 77 and 78 are enabled. Pulses occurring at a frequency eight times greater than the frequency of the echo signals generated in the transducers are applied to each of the divide-by-eight binary counters 77 and 78 through respective ones of inhibit gates 81 and 82 from a frequency synthesizer 83 which derives its input from master oscillator 65. Thus, after a burst of ultrasound has been transmitted along a direction designated by a particular beam number, information is supplied from the phase preset ROM 71 to each of the eight-bit binary counters associated with a respective signal processing channel to develop first and second demodulating signals of the proper phase relationship in respect to the first and second demodulating signals in the other channels to enable coherent demodulation of the echo signals in an initial range zone of the object region. Since all channels receive the same clock pulses, any difference in phase preset counts present at the beginning of a scan will be maintained throughout that scan.

It was pointed out above that in order to provide the proper relative phasing of the first and second demodulating signals in the various signaling processing channels with respect to one another it is necessary to change the phase of each of the first and second demodulating signals with range to maintain this proper relative phasing. The manner in which phasing of the first and second demodulating signals of each channel changes with range is dependent upon beam number, i.e. the angular orientation of the beam, and also on the position of the transducer in relation to the center of the array of transducers will now be described. The amount by which the phase of the first and second demodulating signals of a channel must be changed with range to maintain coherent demodulation of the echo signal can be readily ascertained for the case of a linear array from a consideration of equation 2. The time delay $T_k$ is a function of range R, the particular transducer element under consideration $x_k$, and the angle $\theta$ the beam makes with the normal to the array. The time delay $T_k$ may be converted into a phase variable at the resonant frequency of the transducers by dividing this independent variable by the period of a cycle at the resonant frequency of the transducers. Thus, the phase change required for a given transducer element $x_k$ varies inversely with range R, or time, and directly as the square of cosine $\theta$. The manner in which this relationship is utilized to provide phase slippage with range for each of the signal processing channels will now be explained. The slippage in phase of the first and second demodulating signals of a signal processing channel is provided by deleting or inhibiting a pulse from a sequence of pulses supplied to the divide-by-eight binary counters, such as counters 77 and 78, from the frequency synthesizer 83 through inhibit gates, such as inhibit gate 81 and 82. Each of the inhibit gates is supplied a sequence of bits from the phase slip ROM 72. Whenever there is a change from a bit to its complement, or vice versa, a pulse is inhibited by the inhibit gate from passing through the divide-by-eight binary counter, thus, causing a slippage in phase of 45 degrees of the binary counter. The phase slip ROM 72 is provided with a sequence of words at sequential addresses. The number of bits in each word is equal to the number of channels in the system. Like numbered bits in successive words are provided in sequence to a corresponding inhibit gate in accordance with the sequential counting of the address counter 86. The address counter 86 is connected through a gate 87 to a frequency synthesizer 88 which is under the control of master oscillator 65. The frequency synthesizer 88 provides an output signal of a frequency which is a function of the beam number supplied thereto from beam number controller 62. In particular the frequency of the output signal of frequency synthesizer 88 is proportional to the $\cos^2\theta$ factor of equation 2. The gate 87 blocks the passage of the output signal from the frequency synthesizer 88 to the address counter 86 prior to the occurrence of a start reception signal from start reception circuit 69. On appearance of the start reception signal at gate 87, the output from frequency synthesizer 88 is applied to the address counter 86. The rate at which the address counter 86 runs through the addresses is dependent on the frequency provided by the frequency synthesizer 88. For a beam which is normal to the array the frequency supplied by the frequency synthesizer 88 would have one value corresponding to a particular rate of counting. For a beam off normal by the angle $\theta$ the frequency would be increased by the factor $\cos^2\theta$. Thus, the address counter 86 would be operated at a faster rate and the tractions in bit sign of the words of the phase slip ROM 72 would occur at a faster rate thereby effecting sooner a change in phase of the divide-by-eight binary counter.

The manner in which time delays are provided in each of the I channels and also in each of the Q channels to effect coherent summation of the processed signals will now be described. It was pointed out above that the time delays which must be provided in each of the signal processing channels to effect coherent summation of the processed signals is a function of the angular orientation $\theta$ of the beam or beam number. In order to provide appropriate delays the delay lines in the I channels, such as delay lines 28 and 34, and the delay lines in the Q channel, such as delay lines 44 and 48, are made dependent on the frequencies supplied thereto. When a particular beam number appears on line 74 from beam number controller 62, a set of frequencies are applied to the I and Q delay lines to set the delays therein at the appropriate values to effect coherent summation. Each of the I channel delay lines and also each of the Q channel delay lines provide a steering delay and a dynamic focus delay. The steering delays required are specified for the case of a linear array by equation 1. The dynamic focussing delays required are specified for this case by equation 2. Frequency dependent delay lines which provide frequency dependent delays which meet the requirements of equations 1 and 2 may be of the type shown and described in connection with FIG. 9 in an article entitled, "Ultrasonic Imaging Using Two-Dimensional Transducer Arrays" by W. L. Beaver, et al., appearing in "Cardio-vascular Imaging and Image Processing", Theory and Practice, 1975, Volume 72, published by the Society of Photo-Optical Instrumentation Engineers, Palos Verdos Estates, California. In FIG. 9 of this publication is shown a plurality of signal processing channels for processing echo signals from an array of transducers. Each of the channels includes a first and a second CCD delay line for steering and a third CCD delay line for focussing. The first delay lines vary in length linearly from one side of the array to the other and the second delay lines also vary in length in a complementary fashion. A first clock provides first clocking frequencies to the first delay lines and a second clock provides a second clocking frequencies to the second delay lines. The total number of stages in the first and second delay lines of each channel is the same. Thus, the relative delays of the channels and hence the angle of the receiving beam formed is dependent on the relative magnitudes of the frequency of the first clock and the frequency of the second clock. If these frequencies are the same, the receiving beam would be directed along a normal to the array. When frequency of the first clock is at one extreme value and frequency of the second clock is at another extreme value, the receiving beam is directed along one extreme angle in respect to the normal of the array and vice versa. The third delay lines in each of the channels are provided with a number of stages which varies quadratically from a center channel which has a maximum of stages to a minimum number of stages at the ends thereof. The third delay line is driven by a third clock, the frequency of which is varied over a pulse echo cycle, as required by equation 2, to provide dynamic focussing. Thus, a first plurality of delay lines, each consisting of a first, second and third section, may be utilized as the delay lines for the I channels of the system, and also a second plurality of delay lines, each consisting of a first, second and third section, may be utilized for the delay lines for the Q channels of the system. For each beam number a set of three frequencies is determined, which when supplied to the I and Q delay lines of all of the channels and provides the appropriate delays therein. Data on the three frequencies for each beam number is stored in the delay RAM 73. When RAM 73 is accessed by beam number the data on the set of three frequencies is outputted to the frequency synthesizer 85 which then provides the appropriate set of three frequencies to all of the delay lines of the I and Q channels, including when desired the variation required in the frequency of the third clock during a pulse-echo period to provide dynamic focussing. Such dynamic focussing, however, suffers from distortion errors introduced into the CCD structure by the time variation of the clocks.

The CCD delay line structures are sample data structures which are limited in both band width and time delay accuracy. In prior art systems these limitations severely limit the resonant frequency and, for a given sector angle, the aperture of the transducer array. These prior art systems have therefore been limited either in resolution or the maximum sector angle obtainable, or both. In the present invention the synchronous demodulators provide a means whereby the resonant frequency may be increased without exceeding the band width limitations of the CCD structures. This also permits wider transducer arrays and large sector angles to be utilized. These improvements result in the attainment of increased resolution over a wide field of view of tissue structure features of interest for medical diagnosis or other purposes.

The operation of the apparatus of FIG. 5 will now be described over a pulse-echo cycle or period of operation thereof. Just prior to the application of excitation pulses to the transducers of the array 11 from transmitter 61 a beam number signal from beam number controller 62 appears on line 74. The beam number signal appearing on line 74 is applied to the transmitter 61 and sets the appropriate time delays in the excitation pulses supplied by the transmitter 61 to the transducers of the array 11 to produce a beam of ultrasound directed along a particular direction corresponding to the beam number. The beam number signal is also applied to the phase preset ROM 71 and accesses data addressed thereby. The data is fed to the divide-by-eight binary counters 77 and 78 associated with each signal processing channels to preset the divide-by-eight binary counters to an initial count which corresponds to the angle dependent part of the phase relationship appropriate to the array geometry. This assures that the I and Q waveform generators 75 and 76 are properly phased with respect to one another to enable coherent demodulation of echo signals received by the transducers of the array from the near field of view of the array 11. The beam number signal is also applied to the frequency synthesizer 88 to cause it to develop a phase slip frequency appropriate to the beam number. The beam number signal is also applied to the delay RAM 73 to access the time delay clock frequency data therein which is applied to the frequency synthesizer 85 to develop a set of frequencies, one for each section of the delay lines. The steering delays are developed in the delay lines 28, 34, 44 and 48 corresponding to reception along a receiving beam oriented in the same direction as the transmitting beam. In addition, a dynamic focussing delay is provided in the delay line which is set at one value in the near field and progressively changes as the range from which echoes are received increases thereby enabling coherent summation to be performed on the echo signals processed in the signal processing channels.

Shortly after the excitation pulses from the transmitter 61 develop the burst of ultrasound which emanates from the array 11, a start beam signal is generated and is applied to time gain control circuit 61 which controls the gain of the preamplifier 66 as a function of range to equalize the amplitudes of the received echo signals generated in the transducers of the array. The start beam signal also enables the divide-by-eight binary counters, such as counters 77 and 78, to initiate their count and thus enables the I and Q waveform generators, such as generators 75 and 76, to generate the I and Q waveforms for the various channels of the apparatus to coherently demodulate the various echo signals appearing in these channels. The echo signals are produced first by echoes from the object points in the near field of the array. The steering and dynamic focussing delays of the delay lines of all of the channels are set to provide delay to the demodulated signal appearing at the outputs of the first and second demodulators of all of the channels to occur at the same time and thus be coherently summed in the summation amplifiers.

Shortly after the start beam signal, a start reception signal is developed by the start reception circuit 69 and is applied to gate 87 which is opened and enables the signal appearing at the output of frequency synthesizer 88 to be applied to the address counter 86 causing the latter to count at the rate determined by the frequency of the signal from frequency synthesizer 88. The address counter 86 cycles the addresses of the phase slip ROM 72 at a particular rate which causes the inhibit gates, such as gates 81 and 82, to drop pulses from the frequency synthesizer 83 and hence alter the phasing of the divide-by-eight binary counters. Slipping the phases of the divide-by-eight binary counters enables the phases of the I and Q waveforms of all of the signal processing channels to be maintained at relative values which maintain coherent demodulation of echo signals developed by echoes reflected from object points more distant from the array. Also, during a pulse-echo cycle data supplied by the delay RAM 73, causes the frequency of the clock signal applied to the dynamic focussing sections of the delay lines to be varied to maintain focus on object points more distant from the array. The processed echo signals from more distant object points are coherently summed in the summation amplifiers 35 and 49. The signals from the summation amplifiers 35 and 49 are applied to the circuit 51 which develops an output which is proportional to the square root of the sum of the square of the summation signal $\Sigma I$ and the square of the summation signal $\Sigma Q$. The output of the circuit 51 is referred to as a video signal and has amplitude variations corresponding to echo intensity at various ranges as a function of time. This signal may be applied to various display devices, such as an oscilloscope, to display the amplitude of the signal as a function of time to provide a visual indication of the object point as a function of time or range. When desirable, other combinations of the $\Sigma Q$ and $\Sigma I$ signals may be formed for display purposes.

The pulse-echo cycle for a particular beam may be repeated a number of times and then the same cycle may be executed for other beam numbers in sequence. Thus, video signals are provided enabling a display of object points producing echoes lying in a region scanned by the beam.

Transducers 15 of array 1 may have any resonant frequency. Typically the resonant frequency of the transducers 15 may be between 2.0 to 5.0 megahertz. The frequency of the I and Q waveform generators 75 and 76 and hence the frequency of the divide-by-eight binary counters 77 and 78 would be substantially the same as the resonant frequency of the transducers 15. The frequency of the output of the frequency synthesizer 83 would be eight times the fundamental frequency of the divide-by-eight binary counters, and accordingly, for transducers of resonant frequency of 2.25 megahertz, would be 18 megahertz. Conveniently, the pulses provided by the transmitter could have a duration of time about two microseconds which would produce oscillations of several cycles in the transducer when excited thereby. The repetition rate of the transmitter pulses conveniently may be the order of 3 kilohertz. This frequency is related to the depth of penetration and reflection of ultrasound from object points in the object region into which the ultrasound is directed by the array. The frequency synthesizer 63 provides appropriate frequency information for the generation of pulses of such duration and repetition rate by the transmitter 61. The sequencing of the beam number controller 62 is related to the repetition rate of the excitation pulses and accordingly the frequency synthesizer 64 provides frequencies suitable for such clock operation. The frequency of the output of the frequency synthesizer 88 utilized for phase slip operation lies in the range of the frequency of the frequency of the frequency synthesizer 83. Preferably, this range should not include either the video band of frequencies or the region of frequencies close to the resonant frequency of the transducers. The frequencies developed by the frequency synthesizer 85 utilized for controlling the delays of the delay lines lie generally well above the range of the frequencies of the transducers, that is, of the order of 4.5 megahertz or higher. Master oscillator 65 provides frequencies which may be several times higher than the highest frequency utilized in the system to enable the frequencies developed by the various frequency synthesizers to have the proper values.

Conveniently the linear array 11 may comprise about 50 transducer elements each 0.25 millimeter wide in a longitudinal direction and spaced on about 0.3 millimeter centers in the longitudinal direction.

While the invention has been described in connection with a system incorporating a linear array of transducers, it will be understood that the invention is useful in systems incorporating other than linear arrays in which time delays are required to effect coherent summation of echo-generated signals.

While the invention has been described in connection with imaging of tissue structure within the human body for medical diagnostic purposes, it is apparent that the system may be used for other purposes, such as for fault detection in castings.

While the invention has been described in specific embodiments it will be appreciated that modifications, such as those described above, may be made by those skilled in the art and it is intended by the appended claims to cover all such modifications and changes as fall within the true spirit and scope of the invention.

What I claim as new and desire to secure by Letters Patent of the United States is:

1. An ultrasound imaging system comprising an array of transducers disposed to receive echoes of ultrasound produced by a burst of ultrasound of a predetermined frequency impinging on object points in said object region, each echo from a respective object point producing in said transducers a respective set of electrical signals, one electrical signal in each transducer, the time of occurrence of each of said echo signals being dependent on the distance between a respective transducer and said respective object point, means for demodulating the signals obtained from said transducers including mixing each of said signals with first and second demodulating signals of substantially the same frequency as said predetermined frequency, said second demodulating signal being in phase quadrature to said first demodulating signal, to obtain a plurality of pairs of demodulated signals, means for delaying each pair of demodulated signals by a respective predetermined interval of time corresponding to the distance between a respective transducer and said respective object point to cause each pair of first and second demodulated signals to occur at the same time, means for summing the delayed first demodulated signals to obtain a first sum signal, means for summing the delayed second demodulated signals to obtain a second sum signal, means for forming a resultant signal which is a monotonic function of the sum of the square of said first sum signal and the square of said second sum signal.

2. The system of claim 1 in which said transducers have substantially the same resonant frequency and in which said predetermined frequency is the resonant frequency of said transducers.

3. The system of claim 2 in which transducer means are provided for generating said burst of ultrasound of said predetermined frequency.

4. The system of claim 3 in which said transducers for generating said burst of ultrasound are included in said array of transducers disposed to receive echoes of ultrasound.

5. The system of claim 3 in which each of said transducers for generating said burst of ultrasound are excited by a respective electrical pulse to produce said burst of ultrasound.

* * * * *